(12) United States Patent
Zheng et al.

(10) Patent No.: US 11,967,414 B2
(45) Date of Patent: Apr. 23, 2024

(54) IMAGE RECOGNITION MODEL TRAINING METHOD AND APPARATUS, AND IMAGE RECOGNITION METHOD, APPARATUS, AND SYSTEM

(71) Applicant: Tencent Technology (Shenzhen) Company Limited, Shenzhen (CN)

(72) Inventors: Han Zheng, Shenzhen (CN); Zhongqian Sun, Shenzhen (CN); Hong Shang, Shenzhen (CN); Xinghui Fu, Shenzhen (CN); Wei Yang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 496 days.

(21) Appl. No.: 17/321,219

(22) Filed: May 14, 2021

(65) Prior Publication Data
US 2021/0272681 A1    Sep. 2, 2021

Related U.S. Application Data

(63) Continuation of application No. PCT/CN2020/083489, filed on Apr. 7, 2020.

(30) Foreign Application Priority Data

Apr. 10, 2019 (CN) .......................... 201910284918.6

(51) Int. Cl.
*G16H 30/40* (2018.01)
*G06T 7/00* (2017.01)
*G16H 50/20* (2018.01)

(52) U.S. Cl.
CPC ........... *G16H 30/40* (2018.01); *G06T 7/0012* (2013.01); *G16H 50/20* (2018.01);
(Continued)

(58) Field of Classification Search
CPC ........ G16H 30/40; G16H 50/20; G16H 50/70; G06T 7/0012; G06T 2207/10068;
(Continued)

(56) References Cited

U.S. PATENT DOCUMENTS 10,430,946 B1 * 10/2019 Zhou .................. A61B 5/02007
10,496,884 B1 * 12/2019 Nguyen ............. G06V 30/1916
(Continued)

FOREIGN PATENT DOCUMENTS

CN    106845374 A    6/2017
CN    107368859 A    11/2017
(Continued)

OTHER PUBLICATIONS

Tencent Technology, WO, PCT/CN2020/083489, Jul. 7, 2020, 5 pgs.
(Continued)

*Primary Examiner* — Lewis G West
(74) *Attorney, Agent, or Firm* — Morgan, Lewis & Bockius LLP

(57) ABSTRACT

This application relates to an image recognition model training method, an image recognition method, apparatus, and system. The method includes: obtaining a to-be-recognized image; extracting image feature information of the to-be-recognized image; and obtaining a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least
(Continued)

least annotation information of a lesion category and a lesion position in the strong-label training image sample. According to the lesion position, image feature information of a specific lesion category may be more accurately positioned, thereby improving reliability and accuracy.

20 Claims, 7 Drawing Sheets

(52) U.S. Cl.
CPC ............... *G06T 2207/10068* (2013.01); *G06T 2207/20081* (2013.01); *G06T 2207/20084* (2013.01); *G06T 2207/30096* (2013.01)

(58) Field of Classification Search
CPC . G06T 2207/20081; G06T 2207/20084; G06T 2207/30096; G06T 2207/30028; G06T 2207/30092; G06N 3/045; G06N 3/048; G06N 3/08
See application file for complete search history.

(56) References Cited

U.S. PATENT DOCUMENTS

| | | | | |
|---|---|---|---|---|
| 11,132,792 | B2* | 9/2021 | Zhang | G06N 3/08 |
| 2007/0086660 | A1* | 4/2007 | Ai | G06F 18/2148 |
| | | | | 382/226 |
| 2009/0185731 | A1* | 7/2009 | Ray | G06T 7/12 |
| | | | | 382/131 |
| 2010/0156898 | A1* | 6/2010 | Voros | A61B 5/02007 |
| | | | | 345/419 |
| 2012/0070055 | A1* | 3/2012 | Liu | G06T 7/0016 |
| | | | | 382/131 |
| 2012/0166211 | A1* | 6/2012 | Park | G16H 50/20 |
| | | | | 705/2 |
| 2014/0233826 | A1* | 8/2014 | Agaian | G16H 50/20 |
| | | | | 382/133 |
| 2015/0063667 | A1* | 3/2015 | Sprencz | A61B 6/5217 |
| | | | | 382/128 |
| 2017/0061087 | A1* | 3/2017 | Boroczky | G06F 16/24578 |
| 2017/0200067 | A1* | 7/2017 | Zhou | G06V 30/194 |
| 2018/0000453 | A1* | 1/2018 | Hunter | G06F 3/04883 |
| 2018/0144209 | A1* | 5/2018 | Kim | G06N 3/04 |
| 2018/0247410 | A1 | 8/2018 | Madabhushi et al. | |
| 2019/0015059 | A1* | 1/2019 | Itu | A61B 6/025 |
| 2019/0033315 | A1* | 1/2019 | Bathe | G01N 33/507 |
| 2019/0073569 | A1* | 3/2019 | Ben-Ari | G16H 50/70 |
| 2019/0114771 | A1* | 4/2019 | Zhang | A61B 3/14 |
| 2019/0244348 | A1* | 8/2019 | Buckler | G06V 10/25 |
| 2019/0304092 | A1* | 10/2019 | Akselrod-Ballin | G06N 3/084 |
| 2020/0051257 | A1* | 2/2020 | Sauer | G06T 7/344 |
| 2020/0085382 | A1* | 3/2020 | Taerum | G06T 7/0016 |
| 2020/0380675 | A1* | 12/2020 | Golden | G06T 7/143 |

FOREIGN PATENT DOCUMENTS

| | | |
|---|---|---|
| CN | 107680684 A | 2/2018 |
| CN | 108734195 A | 11/2018 |
| CN | 108961274 A | 12/2018 |
| CN | 108985268 A | 12/2018 |
| CN | 109214386 A | 1/2019 |
| CN | 109359684 A | 2/2019 |
| CN | 109447149 A | 3/2019 |
| CN | 109584218 A | 4/2019 |
| CN | 110009623 A | 7/2019 |
| CN | 110013264 A | 7/2019 |

OTHER PUBLICATIONS

Tencent Technology, IPRP, PCT/CN2020/083489, Sep. 28, 2021, 6 pgs.
Can Gao et al., "Rough Co-Training Model for Incomplete Weakly Labeled Data", Pattern Recognition and Artificial Intelligence, Oct. 2018, vol. 31, No. 10, 8 pgs.
Jiajie Wang et al., "Collaborative Learning for Weakly Supervised Object Detection", Computer Vision and Pattern Recognition, Feb. 10, 2018, Retrieved from the Internet: https://arxiv.org/abs/1802.03531.
Tencent Technology, ISR, PCT/CN2020/083489, Jul. 7, 2020, 3 pgs.

* cited by examiner

IMAGE RECOGNITION MODEL TRAINING METHOD AND APPARATUS, AND IMAGE RECOGNITION METHOD, APPARATUS, AND SYSTEM

CROSS-REFERENCE TO RELATED APPLICATIONS

This application is a continuation application of PCT Patent Application No. PCT/CN2020/083489, entitled "METHOD, DEVICE, AND SYSTEM FOR IMAGE RECOGNITION MODEL TRAINING AND IMAGE RECOGNITION" filed on Apr. 7, 2020, which claims priority to Chinese Patent Application No. 201910284918.6, filed with the State Intellectual Property Office of the People's Republic of China on Apr. 10, 2019, and entitled "IMAGE RECOGNITION MODEL TRAINING METHOD AND APPARATUS, AND IMAGE RECOGNITION METHOD, APPARATUS, AND SYSTEM", all of which are incorporated herein by reference in their entirety.

FIELD OF THE TECHNOLOGY

This application relates to the field of computer technologies, and in particular, to an image recognition model training method and apparatus, and an image recognition method, apparatus, and system.

BACKGROUND OF THE DISCLOSURE

In diagnosis and analysis of various medical images, for example, in diagnosis of a digestive tract disease, an internal image of a body is usually obtained based on a diagnostic tool such as an endoscope, and then related medical personnel determine existence of a lesion and a category of the lesion through human observation, resulting in relatively low recognition efficiency. In some current recognition methods, a large quantity of endoscopic images are obtained, and each image is annotated with a lesion category by the related medical personnel. The annotated images are used as samples for model training, so that based on a trained model, lesion recognition may be performed on another medical image. In this way, whether a lesion occurs is determined, and a diagnosis result is automatically provided.

SUMMARY

Embodiments of this application provide an image recognition model training method and apparatus, and an image recognition method, apparatus, and system, to improve accuracy of lesion prediction.

An embodiment of this application provides an image recognition model training method, including:
  obtaining a training image sample set, the training image sample set comprising at least one strong-label training image sample, the strong-label training image sample being an image sample having strong-label information, and the strong-label information comprising at least annotation information of a lesion category and a lesion position in the image sample;
  extracting image feature information of an image sample in the training image sample set;
  marking image feature information belonging to each preset lesion category based on the image feature information of the image sample and corresponding strong-label information; and training an image recognition model according to a mark result until a strong supervision objective function of the image recognition model converges, to obtain the preset image recognition model, the strong supervision objective function being a loss function of a recognized lesion category and a lesion category in the strong-label information.

An embodiment of this application further provides an image recognition method, including:
  obtaining a to-be-recognized image;
  extracting image feature information of the to-be-recognized image; and
  obtaining a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least annotation information of a lesion category and a lesion position in the strong-label training image sample.

An embodiment of this application provides an image recognition model training apparatus, including:
  an obtaining module, configured to obtain a training image sample set, the training image sample set comprising at least one strong-label training image sample, the strong-label training image sample being an image sample having strong-label information, and the strong-label information comprising at least annotation information of a lesion category and a lesion position in the image sample;
  an extraction module, configured to extract image feature information of each image sample in the training image sample set; and
  a training module, configured to mark image feature information belonging to each preset lesion category based on the image feature information of the image sample and corresponding strong-label information, and train an image recognition model according to a mark result until a strong supervision objective function of the image recognition model converges, to obtain the preset image recognition model, the strong supervision objective function being a loss function of a recognized lesion category and a lesion category in the strong-label information.

An embodiment of this application further provides an image recognition apparatus, including:
  an image obtaining module, configured to obtain a to-be-recognized image;
  an extraction module, configured to extract image feature information of the to-be-recognized image; and
  a recognition module, configured to obtain a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least annotation information of a lesion category and a lesion position in the strong-label training image sample.

An embodiment of this application further provides an image recognition system, including at least: an image acquisition device, an image processing device, and an output device, the image acquisition device being configured to obtain a to-be-recognized image;

the processing device being configured to extract image feature information of the to-be-recognized image, and obtain a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least annotation information of a lesion category and a lesion position in the strong-label training image sample; and the display device being configured to output the lesion category recognition result of the to-be-recognized image.

An embodiment of this application further provides an electronic device, including a memory, a processor, and a plurality of computer programs stored in the memory and executable on the processor, the processor, when executing the programs, implementing steps of either of the image recognition model training method or the image recognition method.

An embodiment of this application further provides a non-transitory computer-readable storage medium, storing a computer program, and the computer program, when executed by a processor, implementing steps of either of the image recognition model training method or the image recognition method.

In the embodiments of this application, image feature information of a specific lesion category can be located more accurately by further using a lesion position rather than based on only annotate information of the lesion category. Therefore, image feature information belonging to a lesion category in a strong label and image feature information not belonging to the lesion category can be more accurately distinguished, thereby reducing noises of training samples, improving training reliability, and enabling more accurately prediction of an image recognition model.

DESCRIPTION OF EMBODIMENTS

Figure 1:
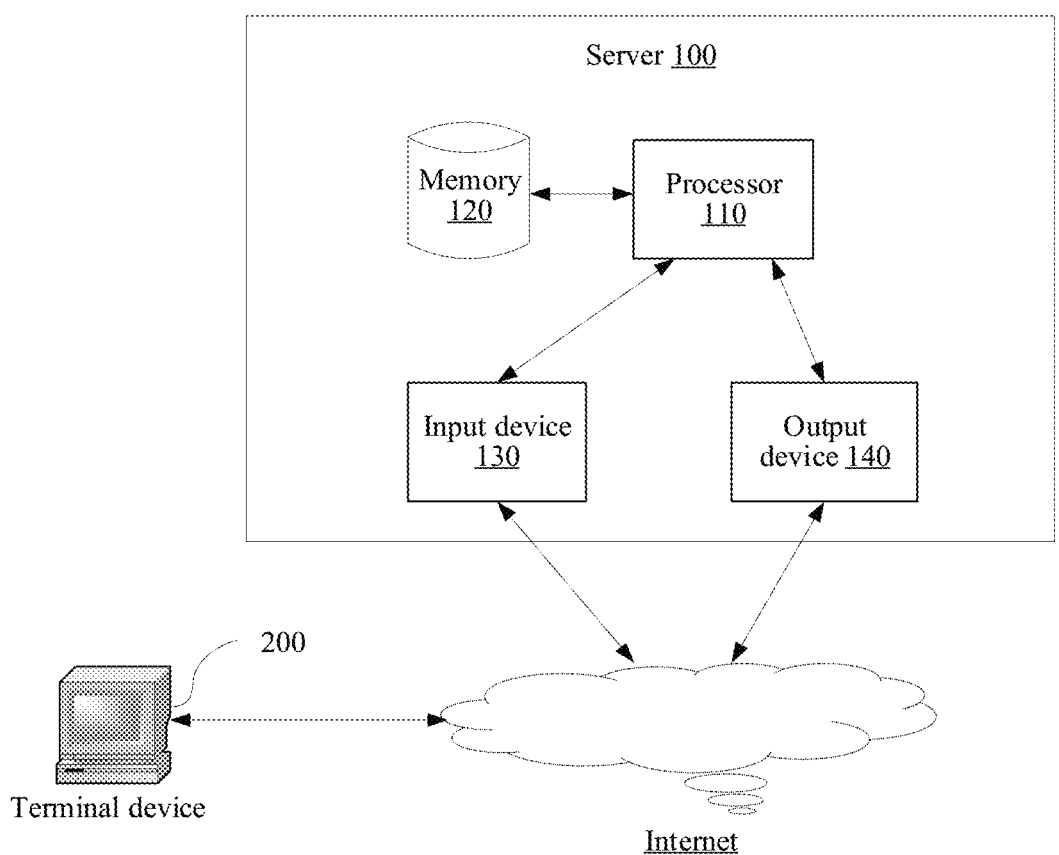
FIG. 1 is a schematic diagram of an application architecture of an image recognition model training method and an image recognition method according to an embodiment of this application.

The following clearly and completely describes the technical solutions in embodiments of this application with reference to the accompanying drawings in the embodiments of this application. Apparently, the described embodiments are some of the embodiments of this application rather than all of the embodiments. All other embodiments obtained by a person of ordinary skill in the art based on the embodiments of this application without creative efforts shall fall within the protection scope of this application.

To facilitate the understanding of the embodiments of this application, the following concepts are briefly introduced.

Weak-label information represents annotation information that only includes information required by a single task. In the embodiments of this application, it indicates that only annotation information of a lesion category is included.

Strong-label information represents annotation information that includes other related information in addition to the information required by the task. In the embodiments of this application, it indicates that at least annotation information of a lesion category and a lesion position is included. The lesion category may represent classifications of various digestive tract lesions, for example, a benign type and a malignant type. The lesion position represents a position of a lesion region that is determined as a specific lesion category.

A deeply supervised object detector (DSOD) algorithm is a detection algorithm in which pre-training is not needed.

An intersection-over-union (IOU) represents a ratio between an intersection of two regions and a union of the two regions, or may be understood as an overlap rate between a candidate box generated by a detection result and an original marker box, that is, a ratio of an intersection to a union of the candidate box and the original marker box, which may be used for evaluating accuracy of detection.

At present, occurrence of a digestive tract disease is increasingly frequent, and an incidence of the digestive tract diseases is high. Even if the disease is temporarily cured, there is a high possibility of recurrence. However, a complete cure rate may be greatly improved if lesions are found as soon as possible and prevention is performed. For diagnosis and analysis of the digestive tract disease, an endoscope is usually used as a diagnostic tool to acquire images of parts such as a stomach and an esophagus. For example, a common endoscope such as a gastroscope enters the esophagus, stomach, and duodenum of a patient from the mouth of the patient. In another example, a colonoscope enters the colorectum of the patient from the anus of the patient for detection. During the detection, images may be archived to facilitate subsequent analysis by related medical personnel. However, the related medical personnel perform observation only through eyes to determine whether there is a lesion and determine a lesion category, resulting in relatively low recognition efficiency and accuracy.

Artificial intelligence (AI) is a theory, a method, a technology, and an application system that uses a digital computer or a machine controlled by a digital computer to simulate, extend, and expand human intelligence, perceive an environment, obtain knowledge, and obtain an optimal result through the knowledge. In other words, AI is a comprehensive technology of computer sciences, attempts to understand essence of intelligence, and produces a new intelligent machine that can react in a manner similar to human intelligence. AI is to study design principles and implementation methods of various intelligent machines, to enable the machines to have functions of perception, reasoning, and decision-making.

The AI technology is a comprehensive discipline, and relates to a wide range of fields including both a hardware-level technology and a software-level technology. Basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning (ML)/deep learning.

The CV is a science that studies how to enable a machine to "see". Furthermore, the CV means that using a camera and a computer to replace human eyes to perform machine vision such as recognition, tracking, and measurement on a target, and further performing graphic processing, so that the computer processes the target into an image more suitable for human eyes to observe, or into an image to be transmitted to an instrument for detection. As a scientific discipline, CV studies related theories and technologies and attempts to establish an AI system that can obtain information from images or multidimensional data. The CV technologies generally include technologies such as image processing, image recognition, image semantic understanding, image retrieval, optical character recognition (OCR), video processing, video semantic understanding, video content/behavior recognition, three-dimensional object reconstruction, a 3D technology, virtual reality, augmented reality, synchronous positioning, and map construction, and further include biological feature recognition technologies such as common face recognition and fingerprint recognition.

ML is a multi-field interdiscipline, and relates to a plurality of disciplines such as the probability theory, statistics, the approximation theory, convex analysis, and the algorithm complexity theory. ML specializes in studying how a computer simulates or implements a human learning behavior to obtain new knowledge or skills, and reorganize an existing knowledge structure, so as to keep improving performance of the computer. ML, as the core of AI, is a basic way to make the computer intelligent, and is applicable to various fields of AI. ML and deep learning generally include technologies such as an artificial neural network, a belief network, reinforcement learning, transfer learning, inductive learning, and learning from demonstrations.

With the research and progress of the AI technology, the AI technology is studied and applied in a plurality of fields, such as a common smart home, a smart wearable device, a virtual assistant, a smart speaker, smart marketing, unmanned driving, automatic driving, an unmanned aerial vehicle, a robot, smart medical care, and smart customer service. It is believed that with the development of technologies, the AI technology will be applied to more fields, and play an increasingly important role.

The solutions provided in the embodiments of this application involve technologies such as CV and ML of AI, and are specifically described by using the following embodiments.

At present, in a manner of using AI to assist in diagnosing a digestive tract disease, a large quantity of endoscopic images are obtained, and each image is annotated with a lesion category by the related medical personnel. The annotated images are used as samples for model training, so that based on a trained model, lesion recognition may be performed on another medical image. In this way, whether a lesion occurs is determined, and a diagnosis result is automatically provided. An annotation of a training image sample is usually consistent with a target task, and is only a single annotation of the same level as the task. For example, if the target task is to determine a property category of a gastric lesion, a lesion category of each image is annotated, resulting in relatively low model accuracy.

Therefore, in the embodiments of this application, an image recognition model training method is provided, strong-label training image samples with more annotation information are used, strong-label information including at least annotation information of a lesion category and a lesion position, and image feature information of image samples in a training image sample set is extracted. The image feature information belonging to each preset lesion category is marked according to the image feature information of the image samples and corresponding strong-label information. According to a mark result, the image recognition model is trained until a strong supervision objective function of the image recognition model converges, to obtain a trained image recognition model. Further, lesion recognition may be performed on a to-be-recognized image based on the trained image recognition model. In this way, because of the richer annotation information, the lesion position may further assist in recognition of the lesion category. Therefore, a better effect may be achieved in the same data amount, and a new training method is provided for the digestive tract endoscopic medical diagnosis method, so that the image recognition model is more accurate, and accuracy of lesion recognition and prediction is improved.

Moreover, in the embodiments of this application, the image recognition model may further be trained by combining the strong-label training image samples and weak-label training image samples. Compared with using only the weak-label training image samples for training, this may further improve prediction accuracy of the image recognition model to some extent.

FIG. 1 is a schematic diagram of an application architecture of an image recognition model training method and an image recognition method according to an embodiment of this application, including a server 100 and a terminal device 200.

The terminal device 200 may be a medical device. For example, a user may view a lesion recognition result of an image based on the terminal device 200.

The terminal device 200 and the server 100 may be connected through an internetwork, to communicate with each other. In some embodiments, a standard communications technology and/or protocol is used for the internetwork described above. The internetwork is usually the Internet, but may alternatively be any other network, including but not limited to, a local area network (LAN), a metropolitan area network (MAN), a wide area network (WAN), or any combination of a mobile, wired, or wireless network, a dedicated network, or a virtual dedicated network. In some embodiments, technologies and/or formats such as the hypertext markup language (HTML) and the extensible markup language (XML) are used for representing data exchanged through the network. In addition, all or some links may be encrypted by using conventional encryption technologies such as a secure socket layer (SSL), transport layer security (TLS), a virtual private network (VPN), and internet protocol security (IPsec). In some other embodiments, custom and/or dedicated data communication technologies may also be used in place of or in addition to the foregoing data communication technologies.

The server 100 may provide various network services for the terminal device 200. The server 100 may be one server, a server cluster including several servers, or a cloud computing center.

In some other embodiments, the server 100 may include a center processing unit (CPU) 110, a memory 120, an input device 130, an output device 140, and the like. The input device 130 may include a keyboard, a mouse, a touchscreen, and the like. The output device 140 may include a display device, such as a liquid crystal display (LCD) or a cathode ray tube (CRT).

The memory 120 may include a read-only memory (ROM) and a random access memory (RAM), and provide program instructions and data stored in the memory 120 for the processor 110. In this embodiment of this application, the memory 120 may be configured to store a program of the image recognition model training method or the image recognition method according to the embodiments of this application.

The processor 110 invokes program instructions stored in the memory 120, and the processor 110 is configured to perform steps of any image recognition model training method or image recognition method in the embodiments of this application according to the obtained program instructions.

In some embodiments, the image recognition model training method or the image recognition method may be performed by the server 100. For example, in the image recognition method, the terminal device 200 may send acquired images of a digestive tract and another body part to the server 100. The server 100 performs lesion recognition on the images, and may return a lesion recognition result to the terminal device 200. The application architecture shown in FIG. 1 applicable to the server 100 side is used as an example for description. In some embodiments, the image recognition method in the embodiments of this application may alternatively be performed by the terminal device 200. For example, the terminal device 200 may obtain a trained image recognition model from the server 100 side, and perform lesion recognition on an image based on the image recognition model, to obtain a lesion recognition result. This is not limited in the embodiments of this application.

The diagram of the application architecture in the embodiments of this application is intended to more clearly describe the technical solutions of the embodiments of this application, and does not constitute a limitation to the technical solutions provided in the embodiments of this application. Certainly, the technical solutions provided in the embodiments of this application are not limited to a service application of digestive tract disease diagnosis and also suitable for similar problems in other application architectures and service applications.

Exemplary description is made by using an example in which the embodiments of this application are applicable to the diagram of the application architecture shown in FIG. 1.

Figure 2:
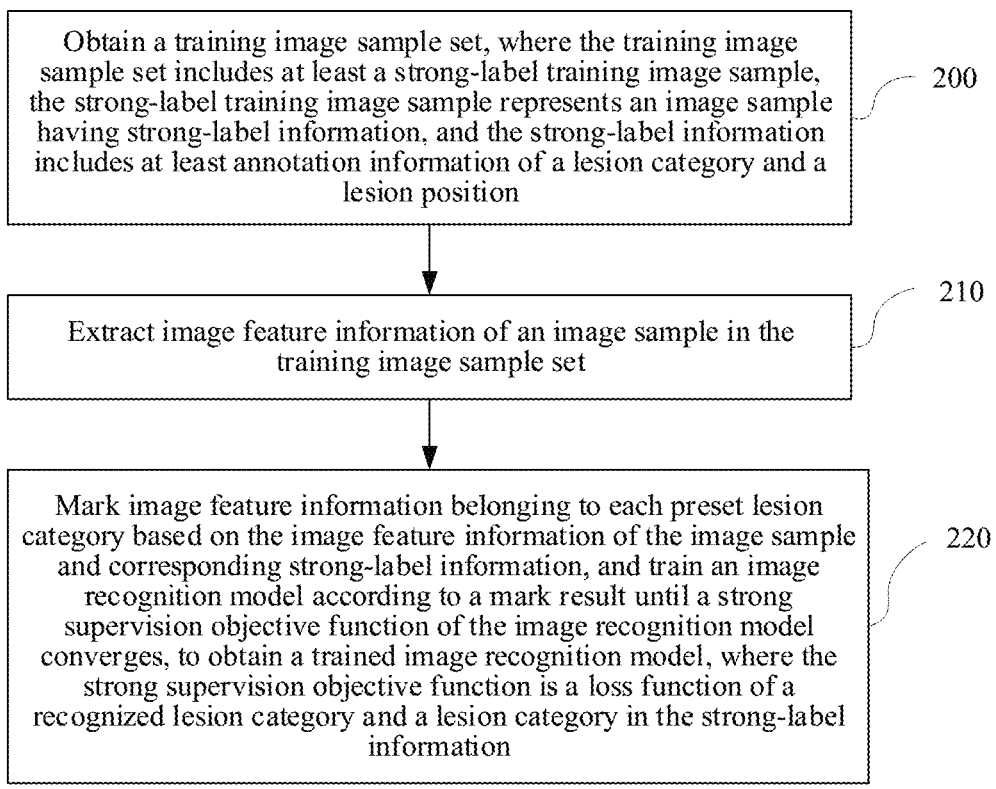
FIG. 2 is a flowchart of an image recognition model training method according to an embodiment of this application.

Based on the foregoing embodiments, FIG. 2 is a flowchart of an image recognition model training method according to an embodiment of this application. The method may be performed by a computing device, for example, the server 100 or the terminal device 200. The method includes the following steps:

Step 200. Obtain a training image sample set.

The training image sample set includes at least a strong-label training image sample. The strong-label training image sample represents an image sample having strong-label information. The strong-label information includes at least annotation information of a lesion category and a lesion position.

Step 210. Extract image feature information of image samples in the training image sample set.

Step 220. Mark image feature information belonging to each preset lesion category based on the image feature information of the image samples and corresponding strong-label information, and train an image recognition model according to a mark result until a strong supervision objective function of the image recognition model converges, to obtain a trained image recognition model.

The strong supervision objective function is a loss function of a recognized lesion category and the lesion category in the strong-label information.

In this embodiment of this application, when the image recognition model is trained, a large quantity of endoscopic images of a digestive tract may be obtained in advance, and a lesion category and a lesion position of a lesion are simultaneously marked by related medical personnel, so that a large quantity of marked strong-label training image samples can be obtained, thereby improving accuracy of lesion recognition by using the strong-label training image sample and the method in this embodiment of this application.

In some embodiments, the training image sample set may further include weak-label training image samples. The weak-label training image sample represents an image sample having weak-label information. The weak-label information includes annotation information of the lesion category. For example, when performing annotation, the related medical personnel may annotate only the lesion category but do not annotate the lesion position, and the sample in this case is the weak-label training image sample.

In this way, if the training image sample set includes samples of two annotation levels, that is, the strong-label training image samples and the weak-label training image samples, the two types of training image samples may be combined to train the image recognition model.

Figure 3:
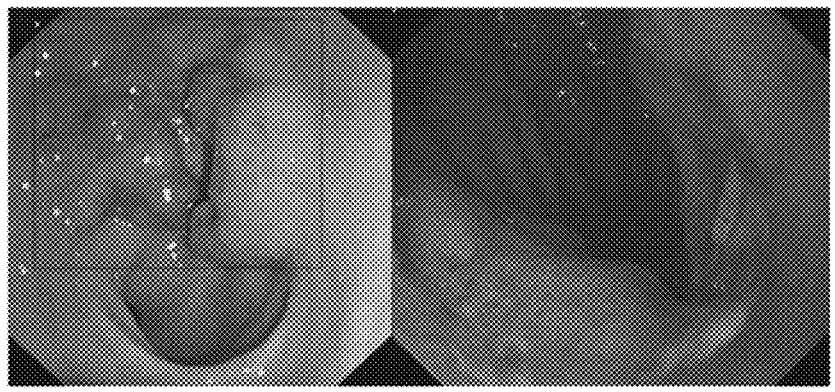
FIG. 3 is a schematic diagram of a strong-label training image sample and a weak-label training image sample according to an embodiment of this application.

FIG. 3 is a schematic diagram of a strong-label training image sample and a weak-label training image sample according to an embodiment of this application. As shown in FIG. 3, the left figure and the right figure are two figures for the same lesion. A block is annotated in the left figure, and may also be referred to as a localization frame, representing the lesion position. A region in the block represents a region in which a lesion belonging to a specific lesion category occurs. However, there is no localization frame in the right figure, and only the annotation information of the lesion category is included. That is, the left figure is the strong-label training image sample, and the right figure is the weak-label training image sample.

This application is intended to improve the accuracy of the lesion prediction of the image recognition model by using more annotation information other than the lesion category. Therefore, the strong-label information is not limited to including the lesion category and the lesion position, and may further include the lesion category and other annotation information. This is not limited in the embodiments of this application.

In some embodiments, step 210 may include the following steps:

(1) Input an image sample in the training image sample set to a neural network.

Considering that recognition of the lesion category is a complex problem, a neural network structure is used for feature extraction. The neural network is, for example, DSOD. Certainly, another deep neural network having the same representation capability may also be used. This is not limited in the embodiments of this application.

(2) Obtain image feature information of a specified dimension that is outputted after the feature extraction is performed on the image sample based on the neural network.

The image feature information is of a P*P*C dimension, P is a specified value, P*P represents that the image sample is equally divided into P*P image blocks horizontally and vertically, and C is a quantity of preset lesion categories. For example, P is any specified natural number.

In this way, the dimension of the image feature information outputted after the feature extraction is performed is P*P*C. For example, if an image is equally divided into 25 image blocks of 5*5, and the quantity of preset lesion categories is 10, finally extracted image feature information is data of a 5*5*10 dimension. Each data point may correspond to one image block, and a value of the data point represents a probability whether the corresponding image block belongs to a specific lesion category.

In some embodiments, to facilitate calculation and improve training efficiency, the image feature information may further be processed by using an activation function, and data of the image feature information is mapped to a specific value range. For example, a sigmoid function is used to map the image feature information to (0, 1). Further, the image feature information processed by using the activation function may be used for training the image recognition model.

In this embodiment of this application, when the image recognition model is trained in step 220, according to annotation statuses of samples in the training image sample set, several implementations below are provided correspondingly.

The first implementation of training the image recognition model in step 220 is: if the training image sample set includes only the strong-label training image sample, marking the image feature information belonging to each preset lesion category based on the image feature information of the image sample and the corresponding strong-label information, and training the image recognition model according to the mark result until the strong supervision objective function of the image recognition model converges, to obtain the trained image recognition model.

For example, the implementation may include the following steps:

S1. Mark the image feature information belonging to the preset lesion category according to the image feature information of the image sample and the corresponding strong-label information, and determine the strong supervision objective function according to the mark result.

In this embodiment of this application, when the training is performed based on the strong-label training image sample, an input of the image recognition model is the strong-label training image sample, that is, an image sample having the strong-label information, an output is the recognized lesion category, and an objective function is the strong supervision objective function.

S2. Optimize the strong supervision objective function until the strong supervision objective function converges, and determine that the training is completed.

That is, the strong supervision objective function is continuously optimized during training, so that the strong supervision objective function is minimized and converges, that is, the training of the image recognition model is determined to be completed.

That is, in this embodiment of this application, the image recognition model can be trained based on only the strong-label training image sample, mark information is richer, and more accurate image feature information belonging to a specific lesion category can be recognized based on the lesion position, so that training information is more reliable, noises are reduced, and the trained image recognition model is more reliable, thereby improving accuracy.

In some embodiments, the manner of determining the strong supervision objective function in step S1 may include the following steps:

S1.1. (1) Mark the image feature information corresponding to the lesion category in the strong-label information.

In some embodiments, for each strong-label training image sample, an overlap rate between each image block in image feature information of the strong-label training image sample and a lesion position is determined according to the lesion position in the strong-label information corresponding to the strong-label training image sample. If the overlap rate is not less than a threshold, a corresponding image block is marked as 1; otherwise, marked as 0, and mark information about whether the strong-label training image sample belongs to a lesion category in the corresponding strong-label information is obtained.

The overlap rate between the image block and the lesion position is determined, and an IUO value of the image block in the image feature information and the lesion position is calculated. The IUO value may represent the overlap rate. If the IUO value is not less than a specific threshold, it indicates that the small image block is more likely to belong to the lesion category, which is marked as 1; otherwise, marked as 0. In this way, mark information that the image block of the strong-label training image sample belongs to the lesion category in the strong-label information is obtained.

In addition, another calculation manner may further be used for determining the overlap rate between the image block and the lesion position. This is not limited in this embodiment of this application. For example, a proportion of the image block to the lesion position is calculated, that is, a proportion of each image block to a localization frame. When the proportion is not less than a specific proportion, the image block is marked as 1, and it is considered that the image block is more likely to belong to the lesion category; otherwise, the image block is marked as 0.

In the embodiments of this application, the image feature information obtained by performing feature extraction on the training image sample is correspondingly referred to as a feature map, and the mark information about whether the strong-label training image sample belongs to the lesion category is correspondingly referred to as a label map, the label map being also corresponding to data of a P*P*C dimension.

Figure 4:
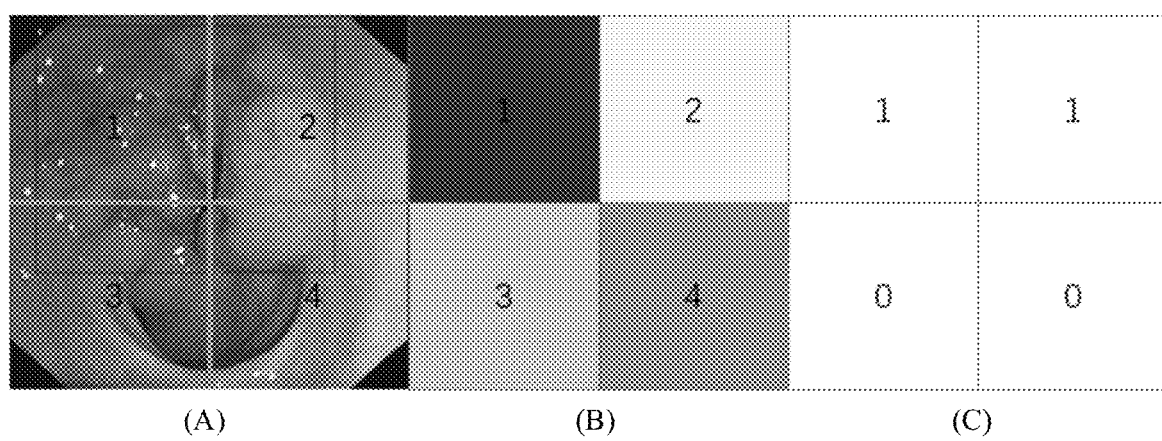
FIG. 4 is a schematic diagram of a feature map and a label map of a strong-label training image sample according to an embodiment of this application.

For example, FIG. 4 is a schematic diagram of a feature map and a label map of a strong-label training image sample according to an embodiment of this application. FIG. 4 (A) is an inputted strong-label training image sample, and a lesion category corresponding to a region of a localization frame in the image sample is A. The image sample is divided into four image blocks, and numbers of the divided image blocks are 1, 2, 3, and 4. FIG. 4 (B) is a corresponding feature map, each point in the feature map corresponds to one image block, and an overlap rate between the image block and the localization frame is calculated. For example, an IOU between the image blocks 1 and 2 and the localization frame is greater than a threshold, an IOU between the image blocks 3 and 4 and the localization frame is less than the threshold. In this case, the image blocks 1 and 2 are marked as 1, and the image blocks 3 and 4 are marked as 0, that is, a label map representing that the image sample belongs to a lesion category A shown in FIG. 4 (C) is obtained.

(2) In some embodiments, image feature information not belonging to the lesion category in the corresponding strong-label information may further be determined, that is, mark information about whether the image feature information of the image sample belongs to another preset lesion category other than the lesion category in the strong-label information is obtained. In some embodiments, the mark information about whether the strong-label training image sample belongs to another preset lesion category other than the lesion category in the strong-label information may be obtained as 0.

That is, for the another lesion category not belonging to the strong-label information, it indicates that in the image sample, there is no lesion region belonging to the another lesion category. In this case, the mark information of the image sample for the another lesion category is 0, that is, a mark corresponding to the image block in the corresponding label map is marked as 0.

For example, for the same lesion, there are three preset lesion categories A, B, and C. If a lesion category in strong-label information of a specific strong-label training image sample is A, mark information that the strong-label training image sample belongs to the lesion categories B and C is 0.

S1.2. Determine the strong supervision objective function according to the image feature information and the mark information about whether the strong-label training image sample belongs to the lesion category.

In some embodiments, a loss function between the mark information and the image feature information is used as the strong supervision objective function.

For example, the strong supervision objective function is:

$$L_{strong} = -((\mathcal{Y}_s \log(p_s) + (1-\mathcal{Y}_s) * \log(1-p_s)))$$

$\mathcal{Y}_s$ represents the strong-label information, $\mathcal{X}_s$, $\mathcal{Y}_s \in X_{strong}$, $X_{strong}$ represents the strong-label training image sample, $p_s = \text{sigmoid}(f(\mathcal{X}_s))$ and $f(\mathcal{X}_s)$ represents the image feature information obtained through feature extraction.

sigmoid $$sigmoid(a) = \frac{1}{1+e^{-a}},$$

where a represents any variable.

The second implementation of training the image recognition model in step 220 is: if the training image sample set includes the strong-label training image sample and the weak-label training image sample, marking the image feature information belonging to each preset lesion category according to the image feature information of the image sample and corresponding strong-label information or weak-label information, and training the image recognition model according to a mark result until a total objective function of the image recognition model converges, to obtain a trained image recognition model. The total objective function is a total loss function of the strong supervision objective function and the weak supervision objective function. The weak supervision objective function is a loss function between a recognized lesion category and the lesion category in the weak-label information.

The second implementation may be applied to a case in which training image samples that may be obtained have different annotation levels. For example, there may be training image samples annotated with only lesion categories, or there may be training image samples marked with both lesion categories and lesion positions. The two types of training image samples may be jointly trained without being distinguished, thereby enriching a quantity of training image samples to some extent. In this case, this embodiment of this application provides a joint training manner based on training image samples with different annotation levels. This manner may include the following steps:

S1. Mark the image feature information belonging to the preset lesion category according to the image feature information of the image sample and the corresponding strong-label information, and determine the strong supervision objective function according to the mark result in a case that the image sample is the strong-label training image sample.

In some embodiments, a manner of determining the strong supervision objective function is the same as the first implementation, and details are not described herein again.

S2. Mark the image feature information belonging to the preset lesion category according to the image feature information of the image sample and the corresponding weak-label information, and determine the weak supervision objective function according to the mark result in a case that the image sample is the weak-label training image sample.

In this embodiment of this application, if the training image sample is the weak-label training image sample, an input of the image recognition model is the weak-label training image sample, that is, an image sample having the weak-label information, an output is the recognized lesion category, and an objective function is the weak supervision objective function.

In some embodiments, the embodiments of this application provide a manner of determining the weak supervision objective function. This manner includes the following steps:

S2.1. Determine, for the weak-label training image sample, a probability that the image block in the image feature information of the weak-label training image sample belongs to the preset lesion category according to the lesion category in the weak-label information corresponding to the weak-label training image sample.

In this way, for each preset lesion category, for each weak-label training image sample, a probability that the weak-label training image sample belongs to the lesion category may be determined, and is referred to as a category feature map. Each category feature map represents a probability that P*P image blocks in the image sample are of the lesion category.

S2.2. Determine a maximum value of the probability that the image block of the weak-label training image sample belongs to the preset lesion category.

For example, there are two preset lesion categories, which are a lesion category A and a lesion category B. A specific weak-label training image sample is divided into four image blocks. Weak-label information of the weak-label training image sample is the lesion category A, and it is assumed that probabilities that the four image blocks of the weak-label training image sample belong to the lesion category A are respectively 0.5, 0.8, 0.2, and 0.3. Because the weak-label information is the lesion category A, the probabilities that the four image blocks of the weak-label training image sample belong to the lesion category A are all 0. For each lesion category, a maximum value of the probability is selected as a probability that the entire weak-label training image sample belongs to the lesion category. That is, a maximum value of the probabilities that the four image blocks of the weak-label training image sample belong to the lesion category A is determined to be 0.8, and to the lesion category B is 0. That is, a probability that the weak-label training image sample belongs to the lesion category A is considered to be 0.8, and to the lesion category B is 0. In this way, a probability of the weak-label training image sample for the lesion category may be obtained.

S2.3 Determine the weak supervision objective function according to a maximum value of a probability that the image block of each weak-label training image sample belongs to the preset lesion category, and the lesion category in the corresponding weak-label information.

In some embodiments, a maximum value of the probability that the image block of the weak-label training image sample belongs to the preset lesion category and a loss function of the lesion category in the weak-label information are calculated, and the loss function is used as a weak supervision objective function.

For example, the weak supervision objective function is:

$$L_{weak} = -((\mathcal{Y}_w \log(p_w) + (1-\mathcal{Y}_w)*\log(1-p_w))$$

$\mathcal{Y}_w$ represents the weak-label information, $\mathcal{X}_w$, $\mathcal{Y}_w \in X_{weak}$ $X_{weak}$ represents the weak-label training image sample, $p_w = \text{sigmoid}(f(\mathcal{X}_w))$ and $f(\mathcal{X}_w)$ represents the image feature information obtained through feature extraction.

S3. Determine a total objective function according to the strong supervision objective function and the weak supervision objective function.

For example, the total objective function is:

$$L_{total} = \lambda L_{strong} + (1-\lambda)L_{weak}$$

where $\lambda$ is a preset weight, and is used for balancing, in the total loss function, proportions of the loss functions of the strong-label training image sample and the weak-label training image sample.

S4. Optimize the total objective function until the total objective function converges, and determine that the training is completed.

In this way, the total objective function converges, to be specific, the strong supervision objective function and the weak supervision objective function both need to converge, and when convergence of both of the strong supervision objective function and the weak supervision objective function is completed, the training process is completed.

In this embodiment of this application, the strong-label training image sample and the weak-label training image sample may be combined to train the image recognition model. In this way, the weak-label training image sample may be allowed to exist to some extent, and all annotation information of the training image sample may be fully used, thereby improving accuracy of the image recognition model.

In some embodiments, because the training is performed mainly based on at least the strong-label training image sample with the lesion category and the lesion position in the embodiments of this application, the trained image recognition model may be used not only for lesion category recognition, but also for lesion position recognition.

Figure 5:
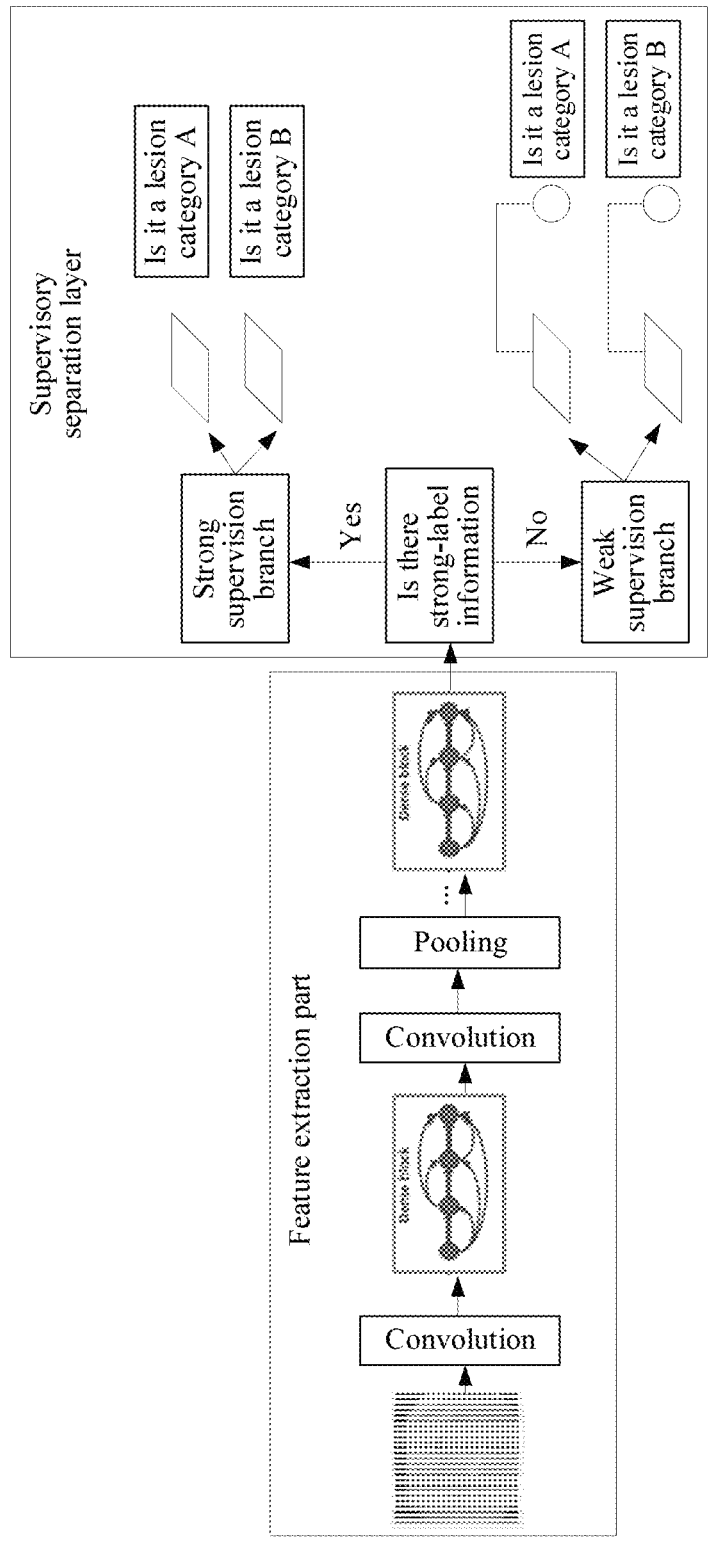
FIG. 5 is a block diagram of a principle of an image recognition model training method according to an embodiment of this application.

Based on the foregoing embodiments, the following describes a specific application scenario, and an example in which the training image sample set includes both the strong-label training image sample and the weak-label training image sample is used for description. FIG. 5 is a block diagram of a principle of an image recognition model training method according to an embodiment of this application.

As shown in FIG. 5, an entire procedure of the image recognition model training method may be divided into two parts.

A first part is a feature extraction part.

Using an example in which feature extraction is performed based on a DSOD model. The feature extraction part shown in FIG. 5 is a basic structure of the DSOD model. Operations such as convolution, dense block, convolution, pooling, and dense block are performed on an image sample in the training image sample set. At the last layer, image feature information of a specified dimension is outputted, and the dimension is P*P*C, representing a feature map of the image sample. Further, a sigmoid function is performed on the feature map, to obtain an inputted feature map of a supervisory separation layer.

For example, the inputted feature map of the supervisory separation layer is: $p_t = \text{sigmoid}(f(\mathcal{X}_t))$, $t \in \{s, w\}$.

$X_{strong}$ represents the strong-label training image sample, $X_{weak}$ represents the weak-label training image sample, $\mathcal{X}_s$, $\mathcal{Y}_s \in X_{strong}$, $\mathcal{X}_w$, $\mathcal{Y}_w \in X_{weak}$ $\mathcal{Y}_s$ represents the strong-label information, $\mathcal{Y}_w$ represents the weak-label information, and $f(\mathcal{X}_t)$ is the image feature information inputted from the last layer through the feature extraction.

A second part is a supervisory separation layer.

In this embodiment of this application, the supervisory separation layer mainly includes a strong supervision branch and a weak supervision branch. Training image samples based on different label information are separately trained through different branches, and whether label information of a training image sample is the strong-label information is determined. If the label information is the strong-label information, the strong-label training image sample is trained in the strong supervision branch. If the label information is not the strong-label information, the weak-label training image sample is trained in the weak supervision branch.

As shown in FIG. 5, there are two preset lesion categories, which are a lesion category A and a lesion category B. The strong supervision branch is to predict a lesion category through training mainly based on a lesion category and a lesion position in strong-label information and determine a strong supervision objective function, and the weak supervision branch is to predict a lesion category through training mainly based on a lesion category in weak-label information and determine a weak supervision objective function. In this way, the strong supervision objective function and the weak supervision objective function are continuously optimized, convergence is achieved, and the training process is completed, thereby achieving an objective of training an image recognition model by synchronously using the strong-label training image sample and the weak-label training image sample.

Figure 6:
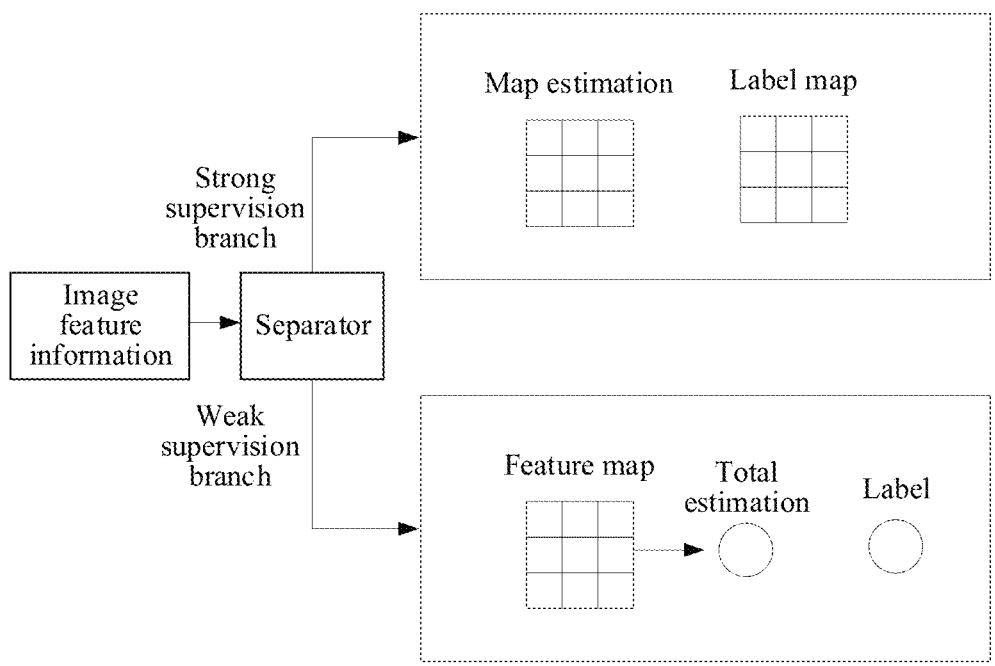
FIG. 6 is a schematic diagram of an implementation logic of a supervisory separation layer in image recognition model training according to an embodiment of this application.

In some embodiments, FIG. 6 is a schematic diagram of an implementation logic of a supervisory separation layer in image recognition model training according to an embodiment of this application. As shown in FIG. 6, according to different annotation levels, image feature information of image samples in a training image sample set enters a strong supervision branch and a weak supervision branch through a separator.

The strong supervision branch is an inputted feature map of the supervisory separation layer. According to the lesion position in the strong-label information, each image block in the inputted feature map is estimated, and a mark of whether the image block belongs to the preset lesion category is obtained, to obtain a corresponding label map. That is, one lesion category corresponds to one label map. A loss function of the label map and the inputted feature map is used as a strong supervision objective function.

It may be learned that there is annotation information of a lesion position in a strong-label training image sample. Therefore, the image block may be estimated and determined. More accurate image feature information representing a lesion can be determined by determining whether the image block belongs to a specific lesion category, thereby improving accuracy of lesion category recognition based on the lesion position.

The weak supervision branch is an inputted feature map of the supervisory separation layer. There is only annotation information of a lesion category but no lesion position in a weak-label training image sample. Therefore, overall estimation is performed only on the inputted feature map. Whether the entire inputted feature map belongs to the preset lesion category is determined, and a corresponding total estimation probability is obtained for the preset lesion category, to obtain a label of the inputted feature map. That is, one lesion category corresponds to one probability. A loss function of the total estimation probability and the lesion category in the weak-label information is used as a weak supervision objective function.

It may be learned that there is only annotation information of a lesion category in the weak-label training image sample. Therefore, during the training, it may only be learned whether image feature information of an entire inputted feature map belongs to a specific lesion category. However, in practice, only image feature information of several small image blocks may conform to image feature information of a corresponding lesion category. In this way, when the weak-label training image sample is trained, some noise image feature information is introduced.

Therefore, in this embodiment of this application, the image recognition model is trained based on the strong-label training image sample, or a combination of the strong-label training image sample and the weak-label training image sample, that is, at least the strong-label training image sample is needed for training. In this way, the lesion position is annotated in the strong-label training image sample, so that during training, not only the annotation information of the lesion category of the strong-label training image sample is used, but position information of the lesion category being determined may further be used. According to the lesion position, the image feature information represented by a lesion can be more accurately determined, and noises are reduced. Compared with using only the weak-label training image sample for training, using the strong-label training image sample for the training of the image recognition model can be more accurate and reliable.

Figure 7:
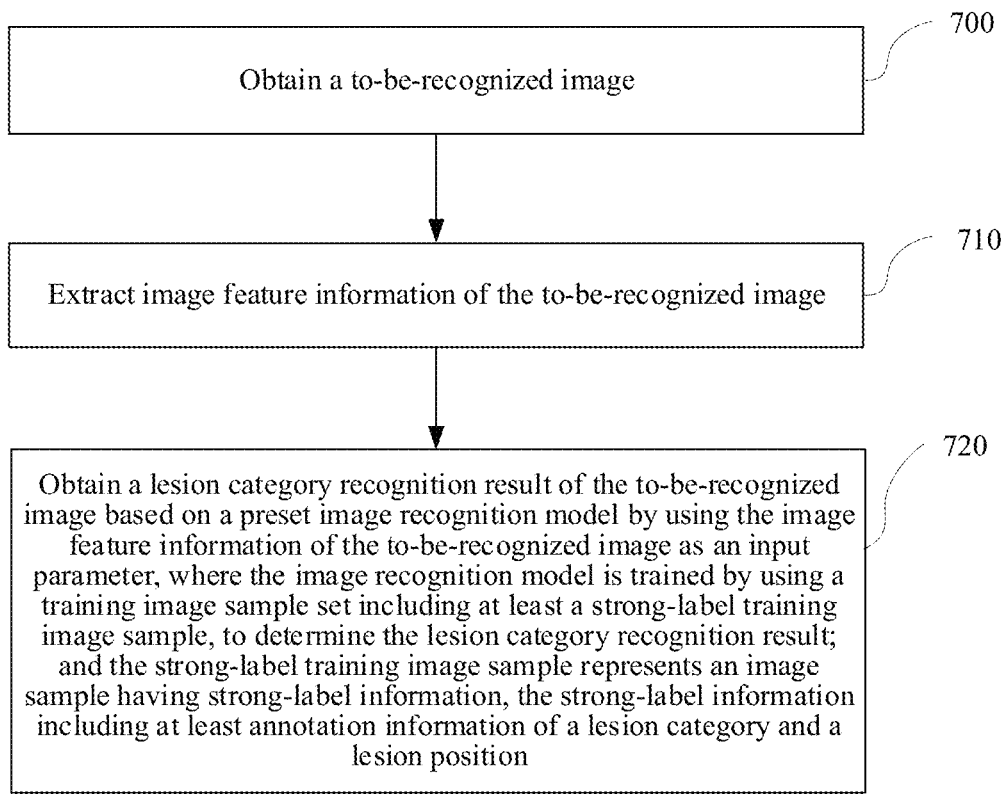
FIG. 7 is a flowchart of an image recognition method according to an embodiment of this application.

Based on the image recognition model training method in the foregoing embodiment, an embodiment of this application further provides an image recognition method. FIG. 7 is a flowchart of an image recognition method according to an embodiment of this application. The method may be performed by a computing device, for example, the server 100 or the terminal device 200. The method may include the following steps:

Step 700. Obtain a to-be-recognized image.

For example, if a trained image recognition model is used for a digestive tract disease, the image recognition model may be configured to recognize a lesion category of the digestive tract disease, and the obtained to-be-recognized image is an acquired digestive tract image.

Step 710. Extract image feature information of the to-be-recognized image.

Step 720. Obtain a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least annotation information of a lesion category and a lesion position in the strong-label training image sample.

In some examples, in step 720, the image recognition model may be configured to determine, and based on a relationship that is between image block feature information of a lesion position and a lesion category and that is determined by using the strong-label training image sample and the strong-label information, whether each image block in the image feature information of the to-be-recognized image belongs to the lesion category, and determine, according to whether each image block belongs to the lesion category, whether the to-be-recognized image belongs to the lesion category as the lesion category recognition result of the to-be-recognized image.

In some examples, in step 720, in addition to using the relationship that is between the image block feature information of the lesion position and the lesion category and that is determined by the strong-label training image sample and the strong-label information, the image recognition model may further be configured to determine, and based on a relationship that is between overall image feature information and a lesion category and that is determined by using a weak-label training image sample and weak-label information, whether the image feature information of the to-be-recognized image belongs to the lesion category. The weak-label information includes only annotation information of the lesion category. When the lesion category recognition result of the to-be-recognized image is determined, whether the to-be-recognized image belongs to the lesion category is determined according to whether the image block belongs to the lesion category and whether the image feature information of the to-be-recognized image belongs to the lesion category.

The image recognition model herein is a model obtained based on the image recognition model training method of the foregoing embodiments. In the embodiments of this application, the image recognition model may be applied to, for example, an endoscope auxiliary diagnostic system, for recognizing the lesion category. Because the image recognition model is trained mainly based on the strong-label training image sample, and is more reliable and accurate, lesion category prediction based on the trained image recognition model is more accurate.

Figure 8:
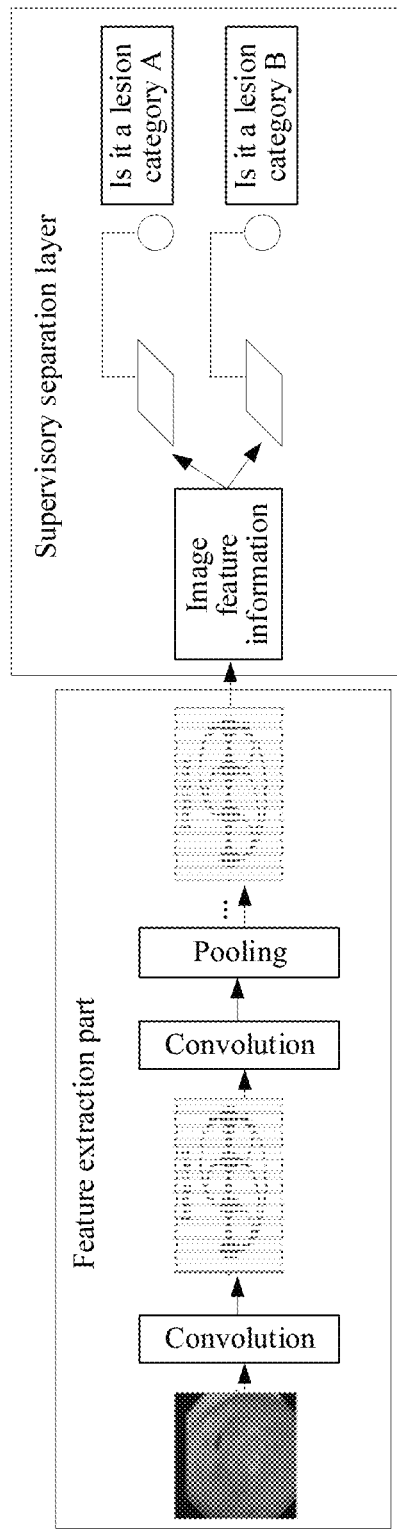
FIG. 8 is a block diagram of a principle of an image recognition method according to an embodiment of this application.

Based on the foregoing embodiments, the following describes a specific application scenario. FIG. 8 is a block diagram of a principle of an image recognition method according to an embodiment of this application.

In this embodiment of this application, the principle of the image recognition method is similar to the principle of the image recognition model training method, and may also be divided into two parts.

A first part is a feature extraction part.

As shown in FIG. 8, DSOD is used as an example. Operations such as convolution, dense block, convolution, pooling, and dense block are performed on a to-be-recognized image to output, at the last layer, image feature information of a specified dimension, and the dimension is P*P*C, representing a feature map of the to-be-recognized image.

In some embodiments, a sigmoid function is performed on the feature map, to obtain an inputted feature map of a supervisory separation layer.

A second part is a supervisory separation layer.

The image feature information obtained through the feature extraction part is inputted to an image recognition model, and the image recognition model determines a lesion category to which the image feature information belongs. For example, there are two preset lesion categories: a lesion category A and a lesion category B. The image recognition model determines whether the image feature information belongs to the lesion category A or the lesion category B, to obtain a final lesion category recognition result.

Figure 9:
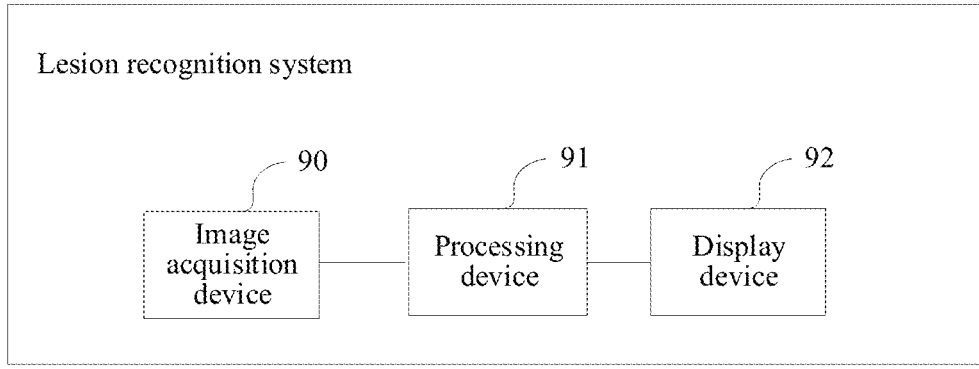
FIG. 9 is a schematic structural diagram of an image recognition system according to an embodiment of this application.

Based on the foregoing embodiments, FIG. 9 is a schematic structural diagram of an image recognition system according to an embodiment of this application.

The image recognition system includes at least an image acquisition device 90, a processing device 91, and a display device 92. In this embodiment of this application, the image acquisition device 90, the processing device 91, and the display device 92 are related medical devices, which may be integrated in the same medical device, or divided into a plurality of devices to connect and communicate with each other to form a medical system for use. For example, for diagnosis of a digestive tract disease, the image acquisition device 90 may be an endoscope, and the processing device 91 and the display device 92 may be computer devices that communicate with the endoscope.

In some embodiments, the image acquisition device 90 is configured to obtain a to-be-recognized image.

The processing device 91 is configured to extract image feature information of the to-be-recognized image, and obtain a lesion category recognition result of the to-be-recognized image based on a preset image recognition model by using the image feature information of the to-be-recognized image as an input parameter. The image recognition model is trained by using a training image sample set including at least a strong-label training image sample, to determine the lesion category recognition result. The strong-label training image sample represents an image sample having strong-label information, and the strong-label information includes at least annotation information of a lesion category and a lesion position.

The display device 92 is configured to output the lesion category recognition result of the to-be-recognized image.

Figure 10:
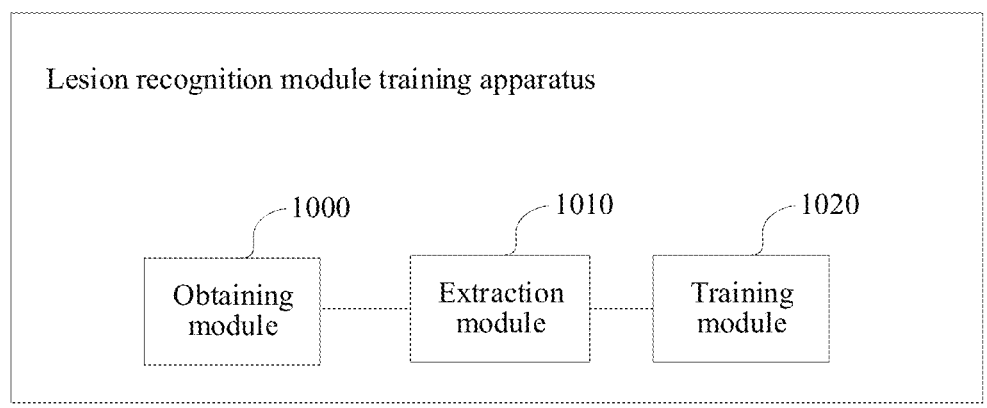
FIG. 10 is a schematic structural diagram of an image recognition model training apparatus according to an embodiment of this application.

Based on the foregoing embodiments, FIG. 10 is a flowchart of an image recognition model training apparatus according to an embodiment of this application, including the following modules: an obtaining module 1000, an extraction module 1010, and a training module 1020.

The obtaining module 1000 is configured to acquire a training image sample set. The training image sample set includes at least a strong-label training image sample. The strong-label training image sample represents an image sample having strong-label information, and the strong-label information includes at least annotation information of a lesion category and a lesion position.

The extraction module 1010 is configured to extract image feature information of an image sample in the training image sample set.

The training module 1020 is configured to mark image feature information belonging to each preset lesion category based on the image feature information of the image sample and corresponding strong-label information, and train an image recognition model according to a mark result until a strong supervision objective function of the image recognition model converges, to obtain a trained image recognition model. The strong supervision objective function is a loss function of a recognized lesion category and a lesion category in the strong-label information.

In some embodiments, the training image sample set further includes a weak-label training image sample. The weak-label training image sample represents an image sample having weak-label information. The weak-label information includes annotation information of a lesion category. The training module 1020 is further configured to mark image feature information belonging to the preset lesion category based on the image feature information of the image sample and corresponding strong-label information or weak-label information, and train the image recognition model according to a mark result until a total objective function of the image recognition model converges, to obtain a trained image recognition model. The total objective function is a total loss function of the strong supervision objective function and the weak supervision objective function. The weak supervision objective function is a loss function of a recognized lesion category and a lesion category in the weak-label information.

In some embodiments, when the image feature information of the image sample in the training image sample set is extracted, the extraction module 1010 is specifically configured to:
input the image sample in the training image sample set to a neural network, and obtain image feature information of a specified dimension that is outputted after feature extraction is performed on the image sample based on the neural network.

In some embodiments, the image feature information is of a P*P*C dimension, P is a specified value, P*P represents that the image sample is equally divided into P*P image blocks horizontally and vertically, and C is a quantity of preset lesion categories.

In some embodiments, when the image feature information belonging to the preset lesion category is marked based on the image feature information of the image sample and the corresponding strong-label information, and the image recognition model is trained according to the mark result until the strong supervision objective function of the image recognition model converges, the training module 1020 is specifically configured to: mark the image feature information belonging to the preset lesion category according to the image feature information of the image sample and the corresponding strong-label information;
determine the strong supervision objective function according to the mark result; and optimize the strong supervision objective function until the strong supervision objective function converges, and determine that the training is completed.

In some embodiments, when the image feature information belonging to the preset lesion category is marked according to the image feature information of the image sample and the corresponding strong-label information or weak-label information, and the image recognition model is trained according to the mark result until the total objective function of the image recognition model converges, the training module 1020 is specifically configured to:

mark the image feature information belonging to the preset lesion category according to the image feature information of the image sample and the corresponding strong-label information, and determine the strong supervision objective function according to the mark result in a case that the image sample is the strong-label training image sample; or mark the image feature information belonging to the preset lesion category according to the image feature information of the image sample and the corresponding weak-label information, and determine the weak supervision objective function according to the mark result in a case that the image sample is the weak-label training image sample;

determine the total objective function according to the strong supervision objective function and the weak supervision objective function; and optimize the total objective function until the total objective function converges, and determine that the training is completed.

In some embodiments, when the image feature information belonging to the preset lesion category is marked according to the image feature information of the image sample and the corresponding strong-label information, and the strong supervision objective function is determined according to the mark result, the training module 1020 is specifically configured to:

determine, for each strong-label training image sample, an overlap rate between the image block in image feature information of the strong-label training image sample and a lesion position according to the lesion position in the strong-label information corresponding to the strong-label training image sample, a corresponding image block being marked as 1 in a case that the overlap rate is not less than a threshold; otherwise, marked as 0, and obtain mark information about whether the strong-label training image sample belongs to the lesion category in the corresponding strong-label information;

obtain mark information about whether the strong-label training image sample belongs to another preset lesion category other than the lesion category in the strong-label information as 0; and determine the strong supervision objective function according to the image feature information and the mark information about whether the strong-label training image sample belongs to each lesion category.

In some embodiments, when the image feature information belonging to the preset lesion category is marked according to the image feature information of the image samples and the corresponding weak-label information, and the weak supervision objective function is determined according to the mark result, the training module 1020 is specifically configured to:

determine, for the weak-label training image sample, a probability that the image block in the image feature information of the weak-label training image sample belongs to the preset lesion category according to the lesion category in the weak-label information corresponding to the weak-label training image sample;

determine a maximum value of the probability that the image block of the weak-label training image sample belongs to the preset lesion category; and determine the weak supervision objective function according to the maximum value of the probability that the image block of each weak-label training image sample belongs to the preset lesion category, and the lesion category in the corresponding weak-label information.

Figure 11:
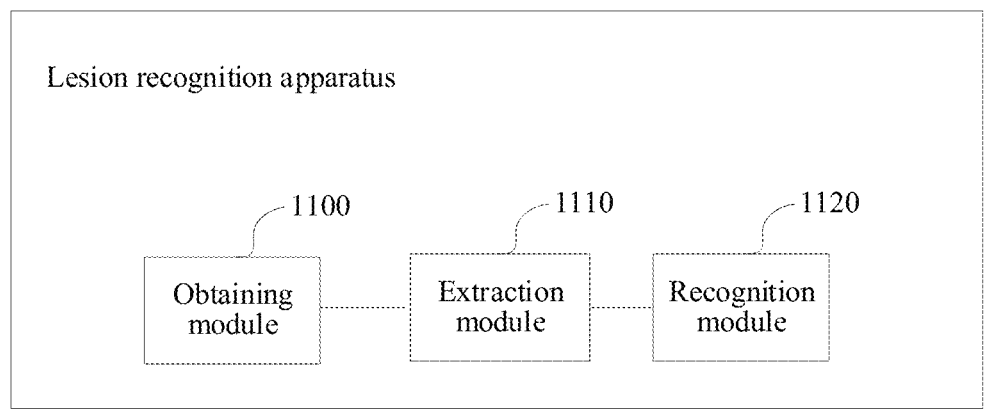
FIG. 11 is a schematic structural diagram of an image recognition apparatus according to an embodiment of this application.

Based on the foregoing embodiments, as shown in FIG. 11, an image recognition apparatus in this embodiment of this application specifically includes:

an obtaining module 1100, configured to obtain a to-be-recognized image;

an extraction module 1110, configured to extract image feature information of the to-be-recognized image; and a recognition module 1120, configured to obtain a lesion category recognition result of the to-be-recognized image by using the image feature information of the to-be-recognized image as an input parameter of a preset image recognition model, the image recognition model being trained by using a training image sample set comprising at least one strong-label training image sample, to determine the lesion category recognition result; and the strong-label training image sample representing an image sample having strong-label information, and the strong-label information comprising at least annotation information of a lesion category and a lesion position in the strong-label training image sample.

In this application, the term "unit" or "module" refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit. Based on the foregoing embodiments, an embodiment of this application further provides an electronic device according to another exemplary implementation. In some embodiments, the electronic device in this embodiment of this application may include a memory, a processor, and a computer program stored in the memory and executable on the processor. The processor, when executing the program, may implement steps of the image recognition model training method or the image recognition method in the foregoing embodiments.

Using an example in which the electronic device is the server 100 in FIG. 1 in this application. The processor in the electronic device is the processor 110 in the server 100, and the memory in the electronic device is the memory 120 in the server 100.

Based on the foregoing embodiments, an embodiment of this application provides a computer-readable storage medium, storing a computer program, the computer program, when executed by a processor, implementing steps of the image recognition model training method or the image recognition method according to any method embodiment described above.

Based on the descriptions of the foregoing implementations, a person skilled in the art may clearly understand that the implementations may be implemented by software in addition to a universal hardware platform, or by hardware. Based on such an understanding, the foregoing technical solutions essentially or the part contributing to the related technology may be implemented in a form of a software product. The computer software product may be stored in a computer-readable storage medium, such as a read-only medium (ROM)/a random access memory (RAM), a magnetic disk, or an optical disc, and includes several instructions for instructing a control device (which may be a personal computer, a server, a network device, or the like) to perform the methods described in the embodiments or some parts of the embodiments.

The foregoing embodiments are merely intended for describing the technical solutions of this application, but not for limiting this application. Although this application is described in detail with reference to the foregoing embodiments, a person of ordinary skill in the art is to understand that they may still make modifications to the technical solutions described in the foregoing embodiments or make equivalent replacements to some technical features thereof, without departing from the spirit and scope of the technical solutions of the embodiments of this application.

What is claimed is:

1. An image recognition method performed by a computing device, the method comprising:
    obtaining a to-be-recognized image;
    extracting image feature information of the to-be-recognized image; and
    obtaining a lesion category recognition result of the to-be-recognized image by using the image feature information of the to-be-recognized image as an input parameter of a preset image recognition model, the image recognition model being trained by using a training image sample set comprising at least one strong-label training image sample and at least one weak-label training image sample, to determine the lesion category recognition result; and the strong-label training image sample representing an image sample having strong-label information, comprising at least annotation information of a lesion category and a lesion position in the strong-label training image sample, and the weak-label training image sample representing an image sample having weak-label information comprising only annotation information of a lesion category.

2. The method according to claim 1, wherein the obtaining a lesion category recognition result of the to-be-recognized image comprises:
    determining, by using the image recognition model, and based on a relationship between a lesion category and image block feature information of a lesion position that is determined from the strong-label training image sample and the strong-label information, whether each image block in the image feature information of the to-be-recognized image belongs to the lesion category; and
    determining whether the to-be-recognized image belongs to the lesion category according to whether the image block belongs to the lesion category.

3. The method according to claim 2, wherein the obtaining a lesion category recognition result of the to-be-recognized image further comprises:
    determining, by using the image recognition model, and based on a relationship between a lesion category and overall image feature information that is determined from the weak-label training image sample and the weak-label information, whether the image feature information of the to-be-recognized image belongs to the lesion category, the weak-label information comprising only annotation information of the lesion category; and
    determining whether the to-be-recognized image belongs to the lesion category according to whether the image block belongs to the lesion category and whether the image feature information of the to-be-recognized image belongs to the lesion category.

4. The method according to claim 1, wherein the preset image recognition model is generated by:
    obtaining a training image sample set, the training image sample set comprising at least one strong-label training image sample, the strong-label training image sample being an image sample having strong-label information, and the strong-label information comprising at least annotation information of a lesion category and a lesion position in the image sample;
    extracting image feature information of each image sample in the training image sample set;
    marking image feature information belonging to each preset lesion category based on the image feature information of the image sample and corresponding strong-label information; and
    training an image recognition model according to a mark result until a strong supervision objective function of the image recognition model converges, to obtain the preset image recognition model, the strong supervision objective function being a loss function of a recognized lesion category and a lesion category in the strong-label information.

5. The method according to claim 4, the method further comprises:
    marking the image feature information belonging to the preset lesion category according to the image feature information of the image sample and corresponding strong-label information or weak-label information; and
    training the image recognition model according to the mark result until a total objective function of the image recognition model converges, to obtain the preset image recognition model, the total objective function being a total loss function of the strong supervision objective function and a weak supervision objective function, and the weak supervision objective function being a loss function of the recognized lesion category and a lesion category in the weak-label information.

6. The method according to claim 5, wherein the extracting image feature information of the image sample in the training image sample set comprises:
    inputting the each image sample in the training image sample set to a neural network; and
    obtaining image feature information of a specified dimension that is outputted after feature extraction is performed on the each image sample based on the neural network.

7. The method according to claim 6, wherein the image feature information is of a P*P*C dimension, P is a specified value, P*P represents that the image sample is equally divided into P*P image blocks horizontally and vertically, and C is a quantity of preset lesion categories.

8. The method according to claim 4, further comprising:
marking the image feature information belonging to the preset lesion category according to the image feature information of the image sample and the corresponding strong-label information;
determining the strong supervision objective function according to the mark result; and
optimizing the strong supervision objective function until the strong supervision objective function converges.

9. The method according to claim 5, further comprising:
marking the image feature information belonging to the preset lesion category according to the image feature information of the image sample and the corresponding strong-label information, and determining the strong supervision objective function according to the mark result in a case that the image sample is the strong-label training image sample; or
marking the image feature information belonging to the preset lesion category according to the image feature information of the image sample and the corresponding weak-label information, and determining the weak supervision objective function according to the mark result in a case that the image sample is the weak-label training image sample;
determining the total objective function according to the strong supervision objective function and the weak supervision objective function; and
optimizing the total objective function until the total objective function converges.

10. A computing device comprising a memory, a processor, and a plurality of computer programs stored in the memory and executable on the processor to perform a plurality of operations including:
obtaining a to-be-recognized image;
extracting image feature information of the to-be-recognized image; and
obtaining a lesion category recognition result of the to-be-recognized image by using the image feature information of the to-be-recognized image as an input parameter of a preset image recognition model, the image recognition model being trained by using a training image sample set comprising at least one strong-label training image sample and at least one weak-label training image sample, to determine the lesion category recognition result; and the strong-label training image sample representing an image sample having strong-label information, comprising at least annotation information of a lesion category and a lesion position in the strong-label training image sample, and the weak-label training image sample representing an image sample having weak-label information comprising only annotation information of a lesion category.

11. The computing device according to claim 10, wherein the obtaining a lesion category recognition result of the to-be-recognized image comprises:
determining, by using the image recognition model, and based on a relationship between a lesion category and image block feature information of a lesion position that is determined from the strong-label training image sample and the strong-label information, whether each image block in the image feature information of the to-be-recognized image belongs to the lesion category; and
determining whether the to-be-recognized image belongs to the lesion category according to whether the image block belongs to the lesion category.

12. The computing device according to claim 11, wherein the obtaining a lesion category recognition result of the to-be-recognized image further comprises:
determining, by using the image recognition model, and based on a relationship between a lesion category and overall image feature information that is determined from the weak-label training image sample and the weak-label information, whether the image feature information of the to-be-recognized image belongs to the lesion category, the weak-label information comprising only annotation information of the lesion category; and
determining whether the to-be-recognized image belongs to the lesion category according to whether the image block belongs to the lesion category and whether the image feature information of the to-be-recognized image belongs to the lesion category.

13. The computing device according to claim 10, wherein the preset image recognition model is generated by:
obtaining a training image sample set, the training image sample set comprising at least one strong-label training image sample, the strong-label training image sample being an image sample having strong-label information, and the strong-label information comprising at least annotation information of a lesion category and a lesion position in the image sample;
extracting image feature information of each image sample in the training image sample set;
marking image feature information belonging to each preset lesion category based on the image feature information of the image sample and corresponding strong-label information; and
training an image recognition model according to a mark result until a strong supervision objective function of the image recognition model converges, to obtain the preset image recognition model, the strong supervision objective function being a loss function of a recognized lesion category and a lesion category in the strong-label information.

14. The computing device according to claim 13, wherein the plurality of operations further comprise:
marking the image feature information belonging to the preset lesion category according to the image feature information of the image sample and corresponding strong-label information or weak-label information; and
training the image recognition model according to the mark result until a total objective function of the image recognition model converges, to obtain the preset image recognition model, the total objective function being a total loss function of the strong supervision objective function and a weak supervision objective function, and the weak supervision objective function being a loss function of the recognized lesion category and a lesion category in the weak-label information.

15. The computing device according to claim 14, wherein the extracting image feature information of each image sample in the training image sample set comprises:
inputting the each image sample in the training image sample set to a neural network; and
obtaining image feature information of a specified dimension that is outputted after feature extraction is performed on the each image sample based on the neural network.

16. The computing device according to claim 13, wherein the plurality of operations further comprise:
- marking the image feature information belonging to the preset lesion category according to the image feature information of the image sample and the corresponding strong-label information;
- determining the strong supervision objective function according to the mark result; and
- optimizing the strong supervision objective function until the strong supervision objective function converges.

17. The computing device according to claim 14, wherein the plurality of operations further comprise:
- marking the image feature information belonging to the preset lesion category according to the image feature information of the image sample and the corresponding strong-label information, and determining the strong supervision objective function according to the mark result in a case that the image sample is the strong-label training image sample; or
- marking the image feature information belonging to the preset lesion category according to the image feature information of the image sample and the corresponding weak-label information, and determining the weak supervision objective function according to the mark result in a case that the image sample is the weak-label training image sample;
- determining the total objective function according to the strong supervision objective function and the weak supervision objective function; and
- optimizing the total objective function until the total objective function converges.

18. A non-transitory computer-readable storage medium storing a plurality of computer programs that, when executed by a processor of a computing device, cause the computing device to perform a plurality of operations including:
- obtaining a to-be-recognized image;
- extracting image feature information of the to-be-recognized image; and
- obtaining a lesion category recognition result of the to-be-recognized image by using the image feature information of the to-be-recognized image as an input parameter of a preset image recognition model, the image recognition model being trained by using a training image sample set comprising at least one strong-label training image sample and at least one weak-label training image sample, to determine the lesion category recognition result; and the strong-label training image sample representing an image sample having strong-label information comprising at least annotation information of a lesion category and a lesion position in the strong-label training image sample, and the weak-label training image sample representing an image sample having weak-label information comprising only annotation information of a lesion category.

19. The non-transitory computer-readable storage medium according to claim 18, wherein the obtaining a lesion category recognition result of the to-be-recognized image comprises:
- determining, by using the image recognition model, and based on a relationship between a lesion category and image block feature information of a lesion position that is determined from the strong-label training image sample and the strong-label information, whether each image block in the image feature information of the to-be-recognized image belongs to the lesion category; and
- determining whether the to-be-recognized image belongs to the lesion category according to whether the image block belongs to the lesion category.

20. The non-transitory computer-readable storage medium according to claim 19, wherein the obtaining a lesion category recognition result of the to-be-recognized image further comprises:
- determining, by using the image recognition model, and based on a relationship between a lesion category and overall image feature information that is determined from the weak-label training image sample and the weak-label information, whether the image feature information of the to-be-recognized image belongs to the lesion category, the weak-label information comprising only annotation information of the lesion category; and
- determining whether the to-be-recognized image belongs to the lesion category according to whether the image block belongs to the lesion category and whether the image feature information of the to-be-recognized image belongs to the lesion category.

* * * * *